United States Patent
Buttermann

[19]
[11] Patent Number: 5,827,328
[45] Date of Patent: Oct. 27, 1998

[54] INTERVERTEBRAL PROSTHETIC DEVICE

[76] Inventor: Glenn R. Buttermann, 1725 Park Ave., Mahtomedi, Minn. 55115

[21] Appl. No.: 753,334

[22] Filed: Nov. 22, 1996

[51] Int. Cl.$^6$ ...................................................... A61F 2/44
[52] U.S. Cl. .............................................................. 623/17
[58] Field of Search ................................ 606/60, 61, 69, 606/70, 71, 53; 623/17, 18, 20

[56] References Cited

U.S. PATENT DOCUMENTS

| | | | |
|---|---|---|---|
| 3,426,364 | 2/1969 | Lumb | 3/1 |
| 4,309,777 | 1/1982 | Patil | 3/1.91 |
| 4,553,273 | 11/1985 | Wu | 623/18 |
| 4,759,769 | 7/1988 | Hedman et al. | 623/17 |
| 4,911,718 | 3/1990 | Lee et al. | 623/17 |
| 4,932,975 | 6/1990 | Main et al. | 623/17 |
| 5,015,255 | 5/1991 | Kuslich | 623/17 |
| 5,059,193 | 10/1991 | Kuslich | 606/61 |
| 5,062,845 | 11/1991 | Kuslich et al. | 606/80 |
| 5,123,926 | 6/1992 | Pisharodi | 623/17 |
| 5,171,278 | 12/1992 | Pisharodi | 623/17 |
| 5,246,458 | 9/1993 | Graham | 623/17 |
| 5,314,477 | 5/1994 | Marnay | 623/17 |
| 5,336,223 | 8/1994 | Rogers | 606/61 |
| 5,360,430 | 11/1994 | Lin | 606/61 |
| 5,375,823 | 12/1994 | Navas | 267/195 |
| 5,390,683 | 2/1995 | Pisharodi | 128/898 |
| 5,397,359 | 3/1995 | Mittelmeier et al. | 623/16 |
| 5,445,639 | 8/1995 | Kuslich et al. | 606/80 |
| 5,458,638 | 10/1995 | Kuslich et al. | 623/17 |
| 5,458,642 | 10/1995 | Beer et al. | 623/17 |
| 5,480,401 | 1/1996 | Navas | 606/61 |
| 5,480,442 | 1/1996 | Bertagnoli | 623/17 |
| 5,489,307 | 2/1996 | Kuslich et al. | 623/17 |
| 5,489,308 | 2/1996 | Kuslich et al. | 623/17 |
| 5,549,679 | 8/1996 | Kuslich | 623/17 |
| 5,571,189 | 11/1996 | Kuslich | 623/17 |
| 5,591,235 | 1/1997 | Kuslich | 623/17 |

FOREIGN PATENT DOCUMENTS

2008851 C1   3/1994   Russian Federation .

OTHER PUBLICATIONS

Von Karin Büttner–Janz et al., "Bandscheibenendoprothetik Entwicklungsweg und gegenwärtiger Stand," *Orthopädie und Traumatologie*, pp. 137–147 (Mar. 1990).

Lee et al., "Development of a Prosthetic Intervertebral Disc" *Spine*, vol. 16, No. 6 Supp., pp. S253–S255 (1991).

Tsuji et al., "Artificial Ceramic Intervertebral Disc Replacement in Cervical Disc Lesion," *J. West. Pac. Orthop. Assoc.*, vol. 27, No. 1, pp. 101–106 (Hong Kong 1990).

Schmiedberg et al., "Isolation and Characterization of Metallic Wear Debris from a Dynamic Intervertebral Disc Prosthesis," *J. of Biomed. Materials Res.*, vol. 28, pp. 1277–1288 (1994).

Steffee, Arthur D., "The Steffee Artificial Disc," *Clinical Efficacy and Outcome in the Diagnosis and Treatment of Low Back Pain*, Chapter 24, pp. 245–257 (1992).

Langrana et al., "Finite–Element Modeling of the Synthetic Intervertebral Disc," *Spine*, vol. 16, No. 6 Supp., pp. S245–S252 (1991).

(List continued on next page.)

*Primary Examiner*—Paul B. Prebilic
*Attorney, Agent, or Firm*—Foley & Lardner

[57] ABSTRACT

An intervertebral prosthetic device for replacement of an intervertebral disc includes a first fixation member for fixation within a first vertebral body and a second fixation member for fixation within a second vertebral body adjacent the first vertebral body. The present prosthetic device also includes a compressible member for positioning between the first and second fixation members. The compressible member has an outer periphery less than or substantially equal to a diameter of a nucleus pulposus of the intervertebral disc. The compressible member thus essentially fits within the annulus fibrosis of the intervertebral disc. The compressible member also has at least one spring that can be pre-loaded to place the annulus fibrosis under tension and to reproduce the mechanical properties of a natural disc.

43 Claims, 7 Drawing Sheets

OTHER PUBLICATIONS

Büttner–Janz et al., "Biomechanics of the SB Charité lumbar intervertebral disc endoprosthesis," *International Orthopaedics (SICOT)*, vol. 13, pp. 173–176 (1989).

Enker et al., "Artificial Disc Replacement," *Spine*, vol. 18, No. 8, pp. 1061–1070 (1993).

Hedman et al., "Design of an Intervertebral Disc Prosthesis," *Spine*, vol. 16, No. 6 Supp., pp. S256–S260 (1991).

Hellier et al., "Wear Studies for Development of an Intervertebral Disc Prosthesis," *Spine*, vol. 17, No. 6 Supp. pp. S86–S96 (1992).

Tie–Sheng et al., "Lumbar Intervertebral Disc Prosthesis," *Chin. Med. J.*, vol. 104, No. 5, pp. 381–386 (1991).

Griffith et al., "A Multicenter Retrospective Study of the Clinical Results of the LINK® SB Charité Intervertebral Prosthesis," *Spine*, vol. 19, No. 16, pp. 1842–1849 (1994).

Kostuik, John P., "The Kostuik Artificial Disc," *Clinical Efficacy and Outcome in the Diagnosis and Treatment of Low Back Pain*, Chapter 25, pp. 259–270 (1992).

Lee et al., "Relative Efficacy of the Artificial Disc versus Spinal Fusion," *Clinical Efficacy and Outcome in the Diagnosis and Treatment of Low Back Pain*, Chapter 23, pp. 237–243 (1992).

Ray, Charles Dean, "The Artificial Disc," *Clinical Efficacy and Outcome in the Diagnosis and Treatment of Low Back Pain*, Chapter 21, pp. 205–225 (1992).

Edeland, H. G., "Some Additional Suggestions for an Intervertebral Disc Prosthesis," *J. Biomed Eng.*, vol. 7, pp. 57–62 (Jan. 1985).

Cinotti et al., "Results of Disc Prosthesis After a Minimum Follow–Up Period of 2 Years," *Spine*, vol. 21, No. 8, pp. 995–1000 (1996).

Urbaniak et al., "Replacement of Intervertebral Discs in Chimpanzees by Silicone–Dacron Implants: A Preliminary Report," *J. Biomed. Mater. Res. Symposium*, vol.7, No. 4, pp. 165–186 (1973).

Fernström, Ulf, "Arthroplasty with Intercorporal Endoprothesis in Herniated Disc and in Painful Disc," *Acta Chir Scand*, vol. 357 Supp., pp. 154–159 (Sweden 1966).

Fassio et al., "Prothères discale en silicone. Etude expèrimentale et premiéres observations cliniques," *La Nouvelle Presse Médicale*, vol. 7, No. 3, p. 207 (1978).

Fernström, U., "Intradiskal Endoprotes av Metall vid Lumbala Och Serricala Diskrupturer," *Nordisk Medicin*, vol. 73, No. 11, pp. 272–273 (1965).

Edeland, H. G., "Suggestions for a Total Elasto–Dynamic Intervertebral Disc Prosthesis," *Biomat., Med. Dev., Art. Org.*, vol. 9, No. 1, pp. 65–72 (1981).

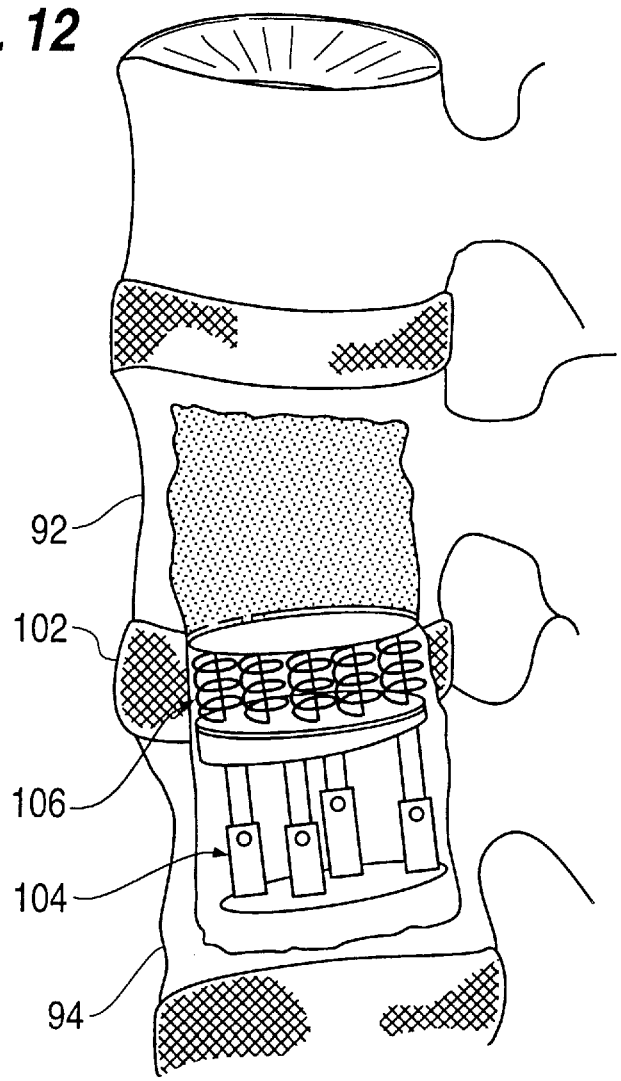

INTERVERTEBRAL PROSTHETIC DEVICE

BACKGROUND OF THE INVENTION

This invention relates to a novel intervertebral prosthetic device. More particularly, this invention relates to an intervertebral prosthetic device that can be implanted to replace a damaged intervertebral disc.

The human spine is a flexible structure comprised of thirty-three vertebrae. Intervertebral discs separate and cushion adjacent vertebrae. The intervertebral discs act as shock absorbers and allow bending between the vertebrae.

An intervertebral disc comprises two major components: the nucleus pulposus and the annulus fibrosis. The nucleus pulposus is centrally located in the disc and occupies 25–40% of the disc's total cross-sectional area. The nucleus pulposus usually contains 70–90% water by weight and mechanically functions like an incompressible hydrostatic material. The annulus fibrosis surrounds the nucleus pulposus and resists torsional and bending forces applied to the disc. The annulus fibrosis thus serves as the disc's main stabilizing structure. Vertebral end-plates separate the disc from the vertebral bodies on either side of the disc.

Individuals with damaged or degenerated discs often experience significant pain. The pain results in part from instability in the intervertebral joint due to a loss of hydrostatic pressure in the nucleus pulposus. Loss of hydrostatic pressure leads to a loss of disc height.

A conventional treatment for degenerative disc disease is spinal fusion. In one such surgical procedure, a surgeon removes the damaged natural disc and then fuses the two adjacent vertebral bones into one piece. The surgeon fuses the vertebral bones by grafting bone between the adjacent vertebrae and sometimes uses metal rods, cages, or screws to hold the graft in place until the graft heals. Other fusion procedures do not require surgical removal of the disc.

Although spinal fusion may alleviate pain associated with degenerative disc disease, it also results in loss of motion at the fused vertebral joint. Lack of motion at the fused site puts additional pressure on the discs above and below the fusion, sometimes causing them to degenerate and produce pain. To remedy the problems associated with spinal fusion, prosthetic devices were developed to replace the damaged disc with a suitable biomechanical equivalent.

Existing prosthetic devices have met with limited success in reproducing the biomechanics of a natural disc. For example, U.S. Pat. No. 4,759,769 to Hedman et. al. discloses a synthetic disc having upper and lower plates hinged together. Although the hinged disc allows forward bending between adjacent vertebrae, the hinged disc does not allow axial compression or lateral flexion. Nor does it allow axial rotation of the vertebral column at the site of the implant. Therefore, the Hedman et. al. device lacks the biomechanics of a natural disc.

Likewise, the prosthetic disc device disclosed in U.S. Pat. No. 4,309,777 to Patil does not replicate natural motion between adjacent discs. The Patil device includes two cups, one overlapping the other and spaced from the other by springs. The cups move only in a single axial dimension. The Patil device thus does not enable natural flexion of the spine in any direction. In addition, the highly constrained motion of the Patil device can lead to high device/tissue interface stresses and implant loosening.

Many synthetic disc devices connect to the vertebral bodies by conventional mechanical attachments, such as pegs or screws, which are known to loosen under cyclic loading conditions. Other synthetic disc devices use plastic or elastomeric components which, over a lifetime, produce debris from wear and possible unknown side effects.

The problems suggested in the preceding are not intended to be exhaustive but rather are among many which tend to reduce the effectiveness of known intervertebral prosthetic devices. Other noteworthy problems may also exist; however, those presented above should be sufficient to demonstrate that currently known devices are amenable to worthwhile improvement.

SUMMARY OF THE INVENTION

Accordingly, it is a general object of the invention to provide an intervertebral disc prosthetic and method for implanting the same which will obviate or minimize difficulties of the type previously described.

More particularly, it is a specific object of the invention to provide an intervertebral prosthetic device which replicates the mechanical properties of a natural intervertebral disc.

It is another object of the invention to provide an intervertebral prosthetic device which restores disc height, defined as the axial distance between vertebrae adjacent the damaged disc, and which duplicates the range of motion of a natural intervertebral joint.

It is still another object of the invention to provide an intervertebral prosthetic device which may be implanted and maintained in stable relation to adjacent vertebrae without conventional mechanical attachments.

It is a further object of the invention to provide an intervertebral disc prosthesis which suffers minimal degradation of the prosthetic material and which produces minimal wear debris under long-term cyclic loading conditions.

It is yet a further object of the invention to provide an intervertebral prosthetic device which axially compresses and thus dissipates energy, may be easily repaired or replaced, may be easily manufactured and utilized by a surgeon, and is durable and modular.

It is yet another object of the invention to provide a method of implanting an intervertebral prosthetic device which stabilizes an operative intervertebral joint and restores the mechanical properties of a degenerated disc.

These objectives are achieved by an intervertebral prosthetic device having a first fixation member, a second fixation member, and a compressible member disposed between them. The first fixation member is implanted within a first vertebral body, and the second fixation member is implanted within a second vertebral body adjacent the first vertebral body.

The first fixation member generally comprises an adjustable member and a support member. The adjustable member preferably has a first plate, a second plate, and at least one adjustment element that extends between the two plates and enables adjustment of the height of the adjustable member along its longitudinal axis. The first plate is operably positioned against subchondral bone of a distant end-plate of the first vertebral body, and the second plate is operably positioned against the support member.

The second fixation member may include both a support member and an adjustable member or, in an alternative embodiment, may include only a support member. In the first embodiment, the adjustable member is structurally similar to the adjustable member of the first fixation member and includes a first plate for positioning against subchondral bone of a distant endplate of the second vertebral body, a second plate for positioning against the support member, and at least one adjustment element extending between the two plates. In the second embodiment, the support member is operably positioned against a near end-plate of the second vertebral body.

One of skill in the art will recognize that, like the second fixation member, the first fixation member may comprise only a support member, depending on the patient's needs. Moreover, the support members are modular. The support members are generally wedge-shaped and may be made in difference sizes to accommodate the angle between adjacent vertebrae at a specific vertebral level. The angle between adjacent vertebrae typically ranges between 3–10 degrees, and, thus the angle created by opposing surfaces of the wedge-shaped support member falls within that same range.

The compressible member has an outer periphery less than or substantially equal to the diameter of the nucleus pulposus of the operative intervertebral disc. In other words, the compressible member is sized to replace the nucleus pulposus of an intervertebral disc and essentially to fit within the annulus fibrosis of the intervertebral disc. The compressible member comprises at least one spring that can be pre-stressed or pre-loaded to place the annulus fibrosis under tension and to reproduce the mechanical properties of a natural disc. Maintaining the annulus fibrosis under tension results in an artificial intervertebral joint that is stable.

The fixation members include a porous surface suitable for bone ingrowth so that the fixation members fuse, or hold, to the vertebrae without requiring conventional mechanical attachments.

Additional objects and advantages of the invention are set forth in the description which follows, and in part will be obvious from the description, or may be learned by practice of the invention. The objects and advantages of the invention may be realized and obtained by means of the instrumentalities and combinations particularly pointed out in the specification and the appended claims.

BRIEF DESCRIPTION OF THE DRAWINGS

The accompanying drawings, which are incorporated in and constitute a part of the specification, illustrate a presently preferred embodiment of the invention, and, together with the general description given above and the detailed description of the preferred embodiment given below, serve to explain the principles of the invention.

FIG. 12 is a schematic, cut-away, side view of a vertebral joint and shows a compressible member implanted in an intervertebral joint;

DETAILED DESCRIPTION OF THE PREFERRED EMBODIMENTS

Figure 1:
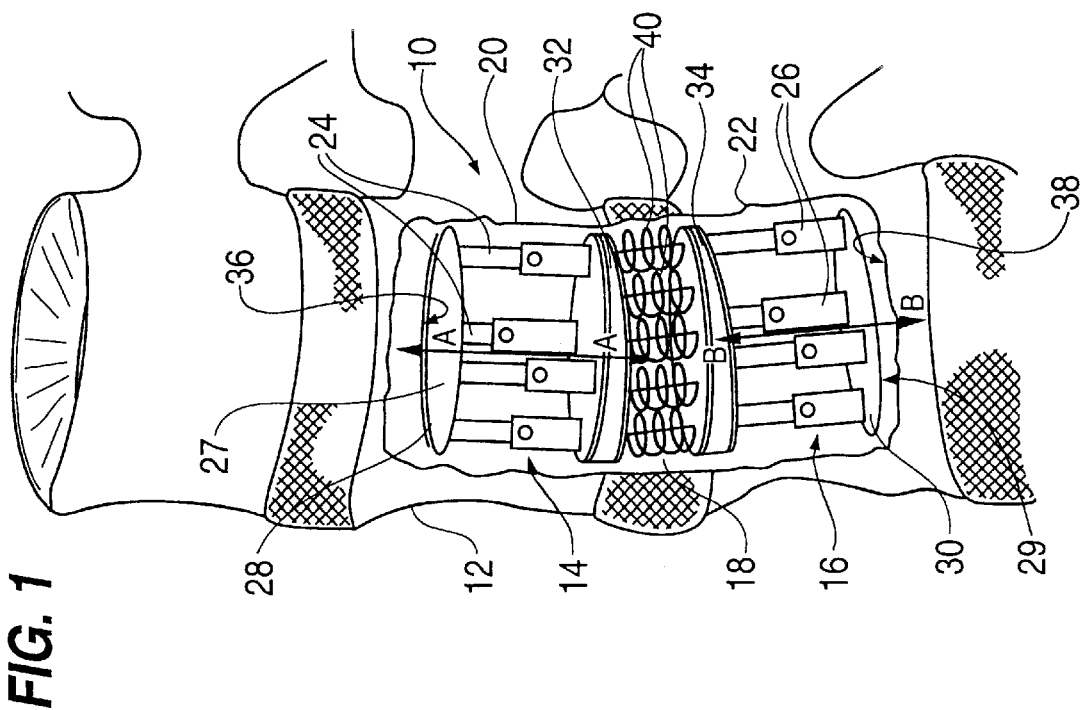
FIG. 1 is a schematic, cut-away, side view of an intervertebral prosthetic device implanted in a spine in accordance with a preferred embodiment of the invention.

Referring now to the drawings, wherein like numerals indicate like parts, and initially to FIG. 1, there will be seen an intervertebral prosthetic device, generally indicated 10, implanted in a spine 12 in accordance with a preferred embodiment of the present invention. The intervertebral prosthetic device 10 is designed to replace a damaged natural disc. The intervertebral prosthetic device 10 has a first fixation member 14, a second fixation member 16, and a compressible member 18 that is positioned between the first fixation member 14 and the second fixation member 16.

The first fixation member 14 is positioned in a first vertebral body 20, and the second fixation member 16 is positioned within a second vertebral body 22 adjacent the first vertebral body 20. Each fixation member 14 and 16 has an adjustable member 28 and 30, respectively, and a support member 32 and 34, respectively. Each fixation member also has a bone-contacting surface, preferably porous, for positioning against subchondral bone of an associated vertebral body. In FIG. 1, a bone-contacting surface 27 of the adjustable member 28 is positioned against the subchondral bone of an end-plate 36 of the superior vertebral body 20, and a bone-contacting surface 29 of the adjustable member 30 is positioned against the subchondral bone of an end-plate 38 of the inferior vertebral body 22. As will be described below, the present intervertebral prosthetic device does not require conventional mechanical attachments, such as pegs or screws, to hold the prosthetic device in place. The intravertebral (i.e., within a vertebral body) positioning of the fixation members maintains the prosthetic device in stable relationship at the operative intervertebral joint.

The adjustable member 28 of the first fixation member 14 has an imaginary first longitudinal axis, shown by dashed line A—A, and adjustment elements 24 that allow adjustment of the height of the adjustable member 28 substantially along its longitudinal axis A—A. In the embodiment shown in FIG. 1, the second fixation member 16 is structurally similar to the first fixation member 14, but inverted. The adjustable member 30 of the second fixation member 16 has a second longitudinal axis, shown by dashed line B—B, and adjustment elements 26 that allow adjustment of the height of the adjustable member 30 substantially along its longitudinal axis B—B.

The compressible member 18 comprises at least one spring and, in a preferred embodiment, comprises a plurality of springs 40. One skilled in the art, however, will recognize that the compressible member may comprise other suitable configurations. For example, the compressible member may comprise a monolithic body made of an biocompatible material compressible in an axial direction, that is, a direction substantially parallel to the spine.

The compressible member 18 is implanted in the region of an excavated nucleus pulposus of the operative intervertebral disc. The compressible member 18 is dimensioned so that the annulus fibrosis of the natural disc is maintained. The present intervertebral prosthetic device restores the mechanical properties of the nucleus pulposus without disrupting the annulus fibrosis. Retention of the annulus fibrosis maintains stability of the intervertebral joint at the implant site. In addition, the annulus fibrosis serves as a boundary for the compressible member and minimizes accidental dislodgement of the prosthetic device.

Significantly, the intervertebral prosthetic device 10 permits at least four degrees of relative motion between the first vertebral body 20 and the second vertebral body 22. These degrees of relative motion include sagittal bending, coronal bending, axial rotation, and axial compression. Moreover, the compressible member permits small increments of translational movement between the vertebral bodies (i.e., fifth and sixth degrees of relative motion, namely anterior-posterior translation and side-to-side, or lateral, translation).

Figure 2:
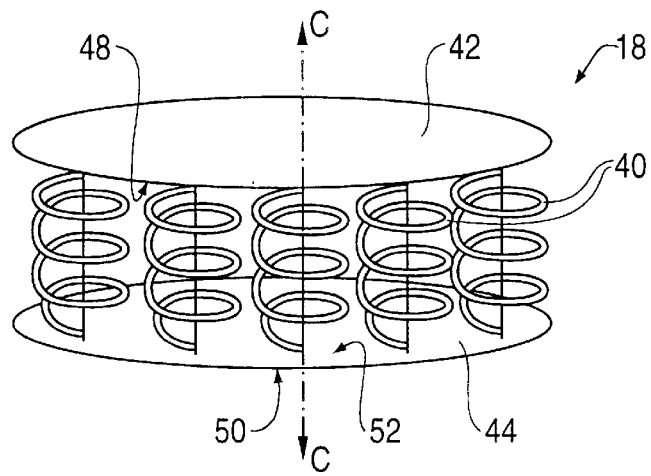
FIG. 2 is a top perspective view of a compressible member of the subject intervertebral prosthetic device.

A preferred embodiment of the compressible member 18 is shown in FIG. 2. The compressible member 18 has a top plate 42, a bottom plate 44, and a plurality of coil springs 40 extending between the top plate 42 and the bottom plate 44. The top plate 42 has a first surface 46, which is connectable to the first fixation member 14, and a second surface 48. The bottom plate 44 also has a first surface 50, which is connectable to the second fixation member 16, and a second surface 52. The springs 40 extend between the second surfaces 48 and 52.

When pre-loaded, as will be explained in more detail below, the compressible member 18 preferably has an axial height of approximately 1.5 cm, greatest at the L45 vertebral level and slightly less at the upper lumbar vertebrae. The coil springs 40 are preferably designed to have non-linear stiffness so that they become stiffer at higher applied loads. The nonlinear stiffness simulates physiological intervertebral stiffness.

One skilled in the art will recognize other embodiments contemplated by the present invention. For example, the compressible member 18 may comprise a plurality of springs extending between, and directly connected to, support members 32 and 34. Alternatively, the compressible member 18 may comprise a single spring with a relatively large coil diameter (not shown) extending between, and directly connected to, the support members 32 and 34. Any spring arrangement may be utilized that achieves sufficient axial compressive force to replicate the biomechanics of the natural disc.

In each embodiment, the compressible member includes an imaginary longitudinal axis, shown by the dashed line C—C in FIG. 2, and an outer periphery in a plane transverse to the longitudinal axis C—C. A largest dimension of the compressible member's outer periphery is less than or substantially equal to the diameter of a nucleus pulposus of the natural intervertebral disc. Put another way, the annulus fibrosis of the natural disc, which is substantially preserved in the implantation procedure, circumscribes the compressible member 18. For example, where the compressible member comprises a plurality of springs, the outer periphery of the compressible member circumscribes the springs, and the largest dimension of that outer periphery may extend to, but does not extend beyond, the nucleus pulposus. In other embodiment, where the compressible member includes a top plate and a bottom plate, and where those plates fit within the annulus fibrosis and extend beyond the outermost portions of the springs, the outer periphery equals the larger of the two plate peripheries. In quantitative terms, the outer periphery of the compressible member preferably ranges between 2.0 cm to 3.0 cm, which approximates the diameter of the nucleus pulposus of a natural intervertebral disc.

Figure 3A:
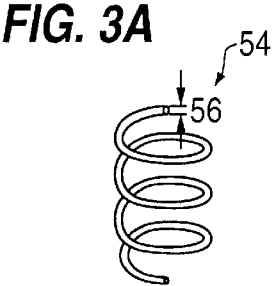
FIGS. 3A–3C are top perspective views of different embodiments of a spring of the compressible member of the subject intervertebral prosthetic device.
Figure 3B:
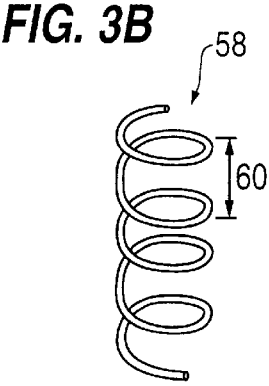
Figure 3C:
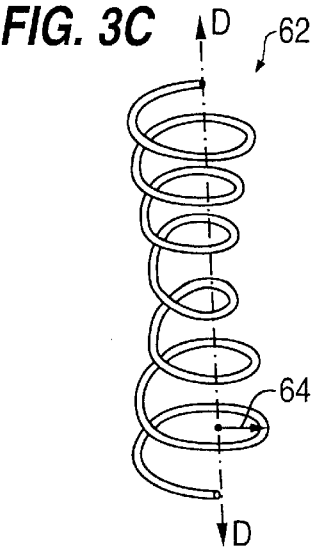

FIGS. 3A–3C show three embodiments of a coil spring designed to possess non-linear stiffness. In the embodiment of FIG. 3A, the coil spring 54 has a variable, or non-uniform, cross-sectional diameter 56. FIG. 3B shows another embodiment in which a coil spring 58 has a variable pitch 60, where the pitch is defined as the distance between successive coils of the spring 58. FIG. 3C shows a third embodiment of a coil spring 62 in which at least two of the spring coils have different radii 64 measured from an imaginary axis D—D extending along the central axis of the spring 62.

Figure 4:
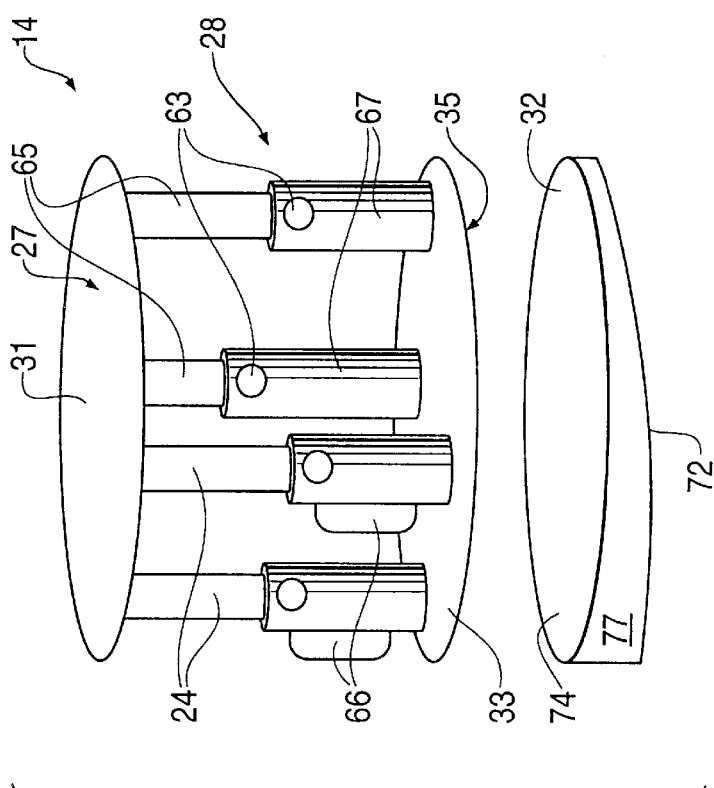
FIG. 4 is a top perspective, partially exploded view of a fixation member of the subject intervertebral prosthetic device and shows an adjustable member and a support member.

FIG. 4 shows a preferred embodiment of the first fixation member 14. In the embodiment shown in FIG. 1, the second fixation member 16 is structurally similar to the first fixation member 14, but inverted. The following discussion thus also applies to the second fixation member 16.

The fixation member 14 comprises an adjustable member, generally indicated 28, and a support member 32. The adjustable member 28 is adjustable in an axial direction by adjustment elements 24. The adjustment elements 24 preferably comprise telescopic struts extending between a first plate 31 and a second plate 33. In a preferred embodiment, the first plate 31 has a bone-contacting surface, such as 27 shown in an operative context in FIG. 1, and the second plate has a surface 35 for positioning against the support member 32. Although the illustrative embodiment shows flat plates 31 and 33, it will be understood by those skilled in the art that these structures need not be flat and may, for example, have undulating surfaces. In fact, in one embodiment, the bone-contacting surface 27 of the first plate 31 is concave to match the contour of the subchondral bone of the associated vertebral body and end plate.

The adjustment elements 24 adjust the distance between the first bone-contacting plate 31 and the second plate 33, thus adjusting the height of the adjustable member 28. A surgeon may adjust the telescopic struts to increase the height of the adjustable member and thus pre-load the compressible member to mechanically reproduce the axial compression absorbed by a nucleus pulposus of a natural disc. Pre-loading the compressible member restores the intervertebral height at the operative joint and restores the function of the annulus fibrosis. The annulus fibrosis load shares with the compressible member which reduces implant/tissue interface stresses.

Figure 5:
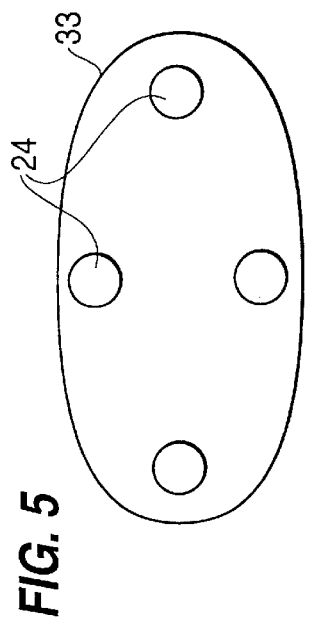
FIG. 5 is a top view of a second plate of the adjustable member.

Each telescopic strut is provided with a lock screw 63 to adjust the length of the strut 24 and hence control the height of the adjustable member. The lock screw 63 may comprise, for example, a pin (not shown) that extends through both the telescoping portion 65 and the housing portion 67 of the strut 24. Each strut 24 is independently adjustable. FIG. 5 shows a top view of the second plate 33 of the adjustable member 28. The adjustment elements 24 preferably are spaced equidistant from each other to enable specific height adjustment of various regions of the adjustable member.

A key feature of the present invention is that controlling the height of the adjustable members 28 and 30, along with selecting an appropriately-sized support member, controls the "disc" height. The disc height is defined as the axial distance between the vertebrae above and below the operative disc. In addition to restoring the disc height, the compressible member 18 acts as a shock absorber to minimize impact loading and, thus, minimize device failure or vertebral fracture.

In a preferred embodiment, the first and second fixation members 14 and 16 have porous portions, such as the bone-contacting surface 27, to permit bone ingrowth. In another embodiment, a biocompatible fabric or suitable material may be wrapped around the fixation members to enable bone ingrowth. The present prosthetic device does not require conventional mechanical attachments, such as pegs or screws, to hold the prosthesis permanently in place. The present prosthetic device, however, may include mechanical or other attachments to supplement the porous portions of the fixation members and to temporarily fix the prosthetic device in place until bone ingrowth has occurred.

To further promote bone ingrowth, the adjustment elements 24 may include fins 66 extending outward from an exterior surface of the element 24, as shown in FIG. 4. The fins 66 increase the surface area of the fixation member 14 to which bone may attach. Preferably, these fins 66 are located on the adjustment elements that are positioned on the anterior side of the adjustable member 28. The present prosthetic device also may include protuberances (not shown) on the bone-contacting surface of the adjustable members to increase the surface area of the porous portion of the fixation members and, thus, encourage bone ingrowth.

Figure 6:
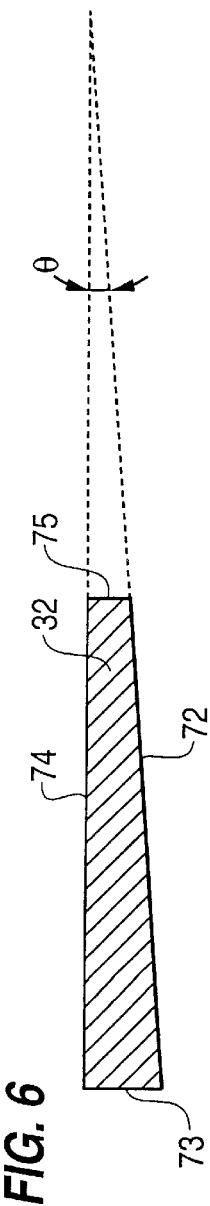
FIG. 6 is a side view, in cross-section, of the support member.

FIG. 6 shows a cross-section of support member 32. The support member 32 has a first surface 72 that operably faces away from the compressible member 18 and a second surface 74 that operably faces towards the compressible member 18. The first and second surfaces 72 and 74 are oblique so that a circumferential surface 77 around the support member 32 varies in width, as shown in FIG. 4. The support member 32 thus is wedge-shaped. In other words, the support member 32 preferably tapers from a maximum thickness at one side 73 to a minimum thickness at an opposite side 75. Generally, the support member 32 is thicker on the side of the fixation member 14 placed anteriorly in a patient's spine to account for the spine's natural curvature.

The support members are constructed with various thicknesses and with various angled surfaces, depending upon the vertebral level of the operative intervertebral joint. An angle Θ shown in FIG. 6 ranges between 3–10 degrees. The support members are shaped to maintain sagittal alignment. Maintaining sagittal alignment avoids nonuniform loading of the compressible member and avoids early fatigue failure of that member.

Figure 7:
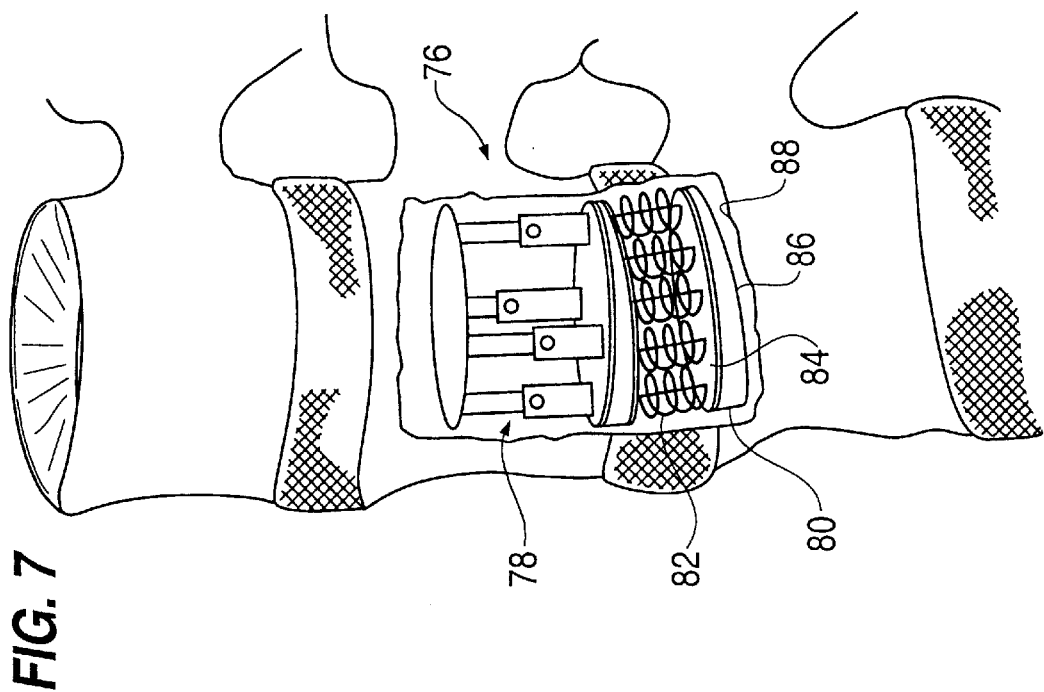
FIG. 7 is a schematic, cut-away, side view of an intervertebral prosthetic device implanted in a spine in accordance with another preferred embodiment of the invention.

FIG. 7 shows another embodiment of the present intervertebral prosthetic device, generally indicated 76, which comprises a first fixation member 78, a second fixation member 80, and a compressible member 82. The compressible member 82 is positioned between the first and second fixation members 78 and 80. The second fixation member comprises a wedge-shaped support member with an upper surface 84 that attaches to the compressible member 82 and a lower surface 86 that rests upon subchondral bone of a near end-plate 88 of an inferior vertebral body. In this embodiment, adjustment of the first fixation member 78 pre-loads the compressible member 82 to an appropriate extent. This embodiment is particularly suited for young patients. Also, in this embodiment, a lower surface 86 of the support member 80 has a slightly convex shape to match the natural contour of the near end-plate of the inferior vertebral body. The surface 86 is preferably composed of a porous material.

As evident from the embodiments of FIGS. 1 and 7, the present intervertebral prosthetic device has a modular design so that the prosthesis may be sized to the patient's anatomy and designed for the patient's condition. The modular design also enables replacement of individual components of the prosthesis (i.e., an adjustable member, a support member, or a compressible member), rather than replacement of the entire prosthesis should one component fail. The compressible member is preferably attached to the fixation members by mechanical attachments, such screws, rather than bone cement so that a surgeon may easily replace damaged or worn components.

Moreover, because the present prosthetic device has no ball bearings, rollers, or hinges, it produces little wear debris. And, because the present prosthetic device need not include plastic polymers or elastomeric components, the present prosthetic device does not degrade under long-term cyclic loading conditions.

The present prosthetic device comprises biocompatible metallic materials, preferably a titanium alloy having, for example, 4% vanadium and 6% aluminum. Persons of skill in the art will recognize other suitable materials, for example, a cobalt-chromium alloy, such as alloy number 301. Alternatively, the present prosthetic device, with the exception of the springs of the compressible member, may comprise a ceramic material, such as aluminium oxide and zirconium oxide. The porous surfaces of the bone-contacting member and support member may be coated with hydroxyapatite or bioactive proteins (e.g., bone morphogenic protein) to encourage bone ingrowth.

Figure 8:
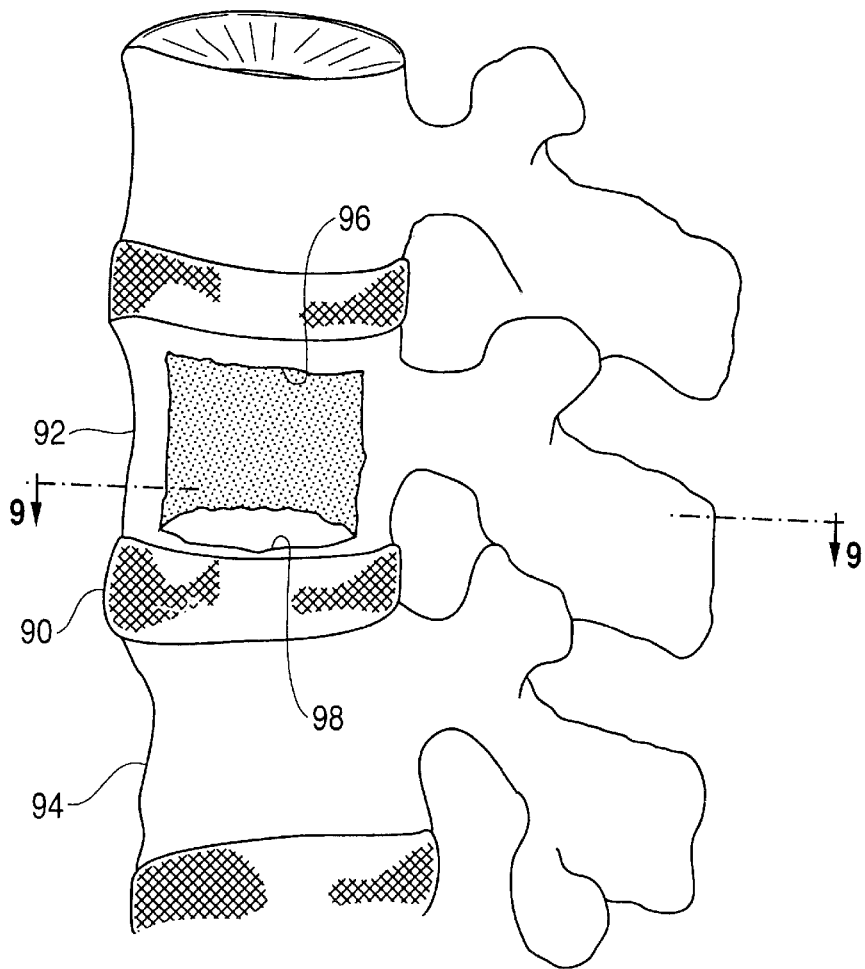
FIG. 8 is a schematic, cut-away, side view showing subchondral bones of a superior vertebral body after a partial vertebrectomy.
Figure 9:
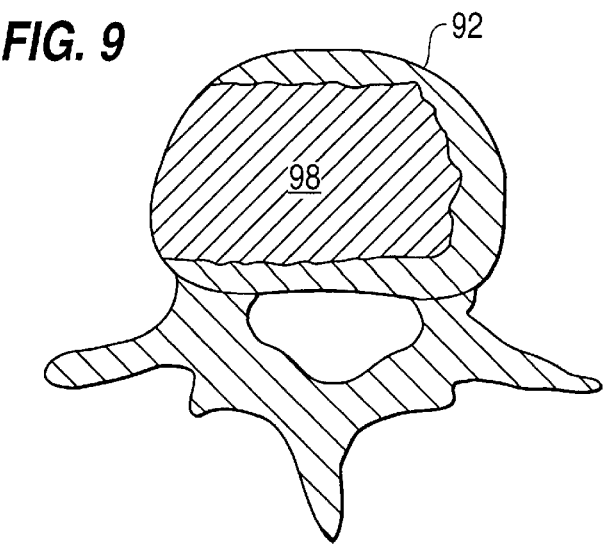
FIG. 9 is a sectional view of a vertebrae after a partial vertebrectomy, as taken along line 9—9 of FIG. 8.

A method of intervertebral disc replacement now will be described in connection with FIGS. 8–14. FIG. 8 shows a pathological intervertebral disc 90 located between a superior vertebral body 92 and an inferior vertebral body 94. Prior to implantation, a surgeon performs a partial vertebrectomy to excise bone matter from the superior vertebral body 92 for receipt of a fixation member. The partial vertebrectomy creates a cavity bounded by subchondral bone of a distant end-plate 96 and subchondral bone of a near end-plate 98 of the superior vertebral body 92. FIG. 9 shows a cross-sectional view of the superior vertebral body 92 after the partial vertebrectomy, as taken along line 9—9 in FIG. 8.

Figure 11:
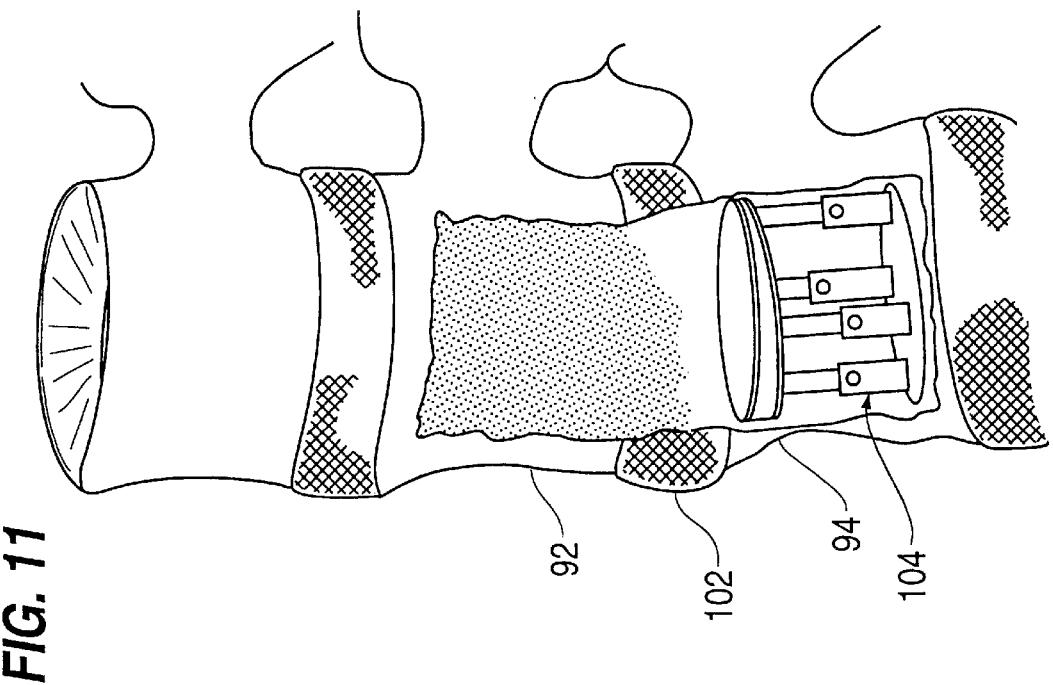
FIG. 11 is a schematic, cut-away, side view of a vertebral joint and shows a fixation member, including an adjustable member and a support member, implanted in an inferior vertebral body.
Figure 10:
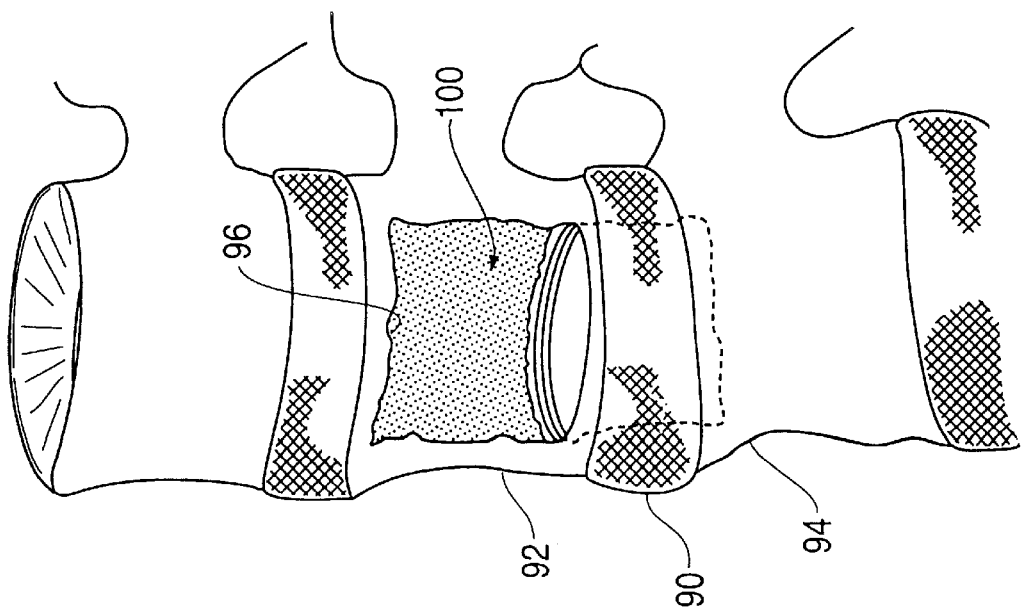
FIG. 10 is a schematic, cut-away, side view of a vertebral joint area after a partial vertebrectomy and excision of a nucleus pulposus of a natural disc.

The surgeon next excises the nucleus pulposus of the damaged disc to create a cavity 100, as shown in FIG. 10, for receipt of the compressible member. The annulus fibrosis 102, seen in FIG. 11, is maintained. The surgeon may perform a partial vertebrectomy on the inferior vertebral body or may excise cartilage matter only to the near end-plate, depending upon whether the surgeon implants the embodiment shown in FIG. 1 or the embodiment shown in FIG. 7, respectively. The following description details implantation of the prosthesis shown in FIG. 1; however, one of skill in the art would understand how to modify the procedure described below to implant the prosthesis of FIG. 7.

Upon completion of the partial vertebrectomies, the surgeon implants a fixation member 104 into the inferior vertebral body 94, as shown in FIG. 11. The surgeon selects a support member with an appropriate thickness to accommodate the angulation at the operative intervertebral levels. The surgeon then inserts a compressible member 106 into the cavity formerly containing the nucleus pulposus of the damaged disc and connects it to the fixation member 104, as shown in FIG. 12. The compressible member 106 and the fixation member 104 may be connected by conventional attachment members, such as screws, or by biocompatible cement or a suitable adhesive composition. Finally, the surgeon implants another fixation member, similar to the one implanted in the inferior vertebral body 94, yet inverted, in the superior vertebral body 92. Connection of that fixation member to the compressible member 106 forms an intervertebral prosthetic device like the one shown in FIG. 1.

Figure 13:
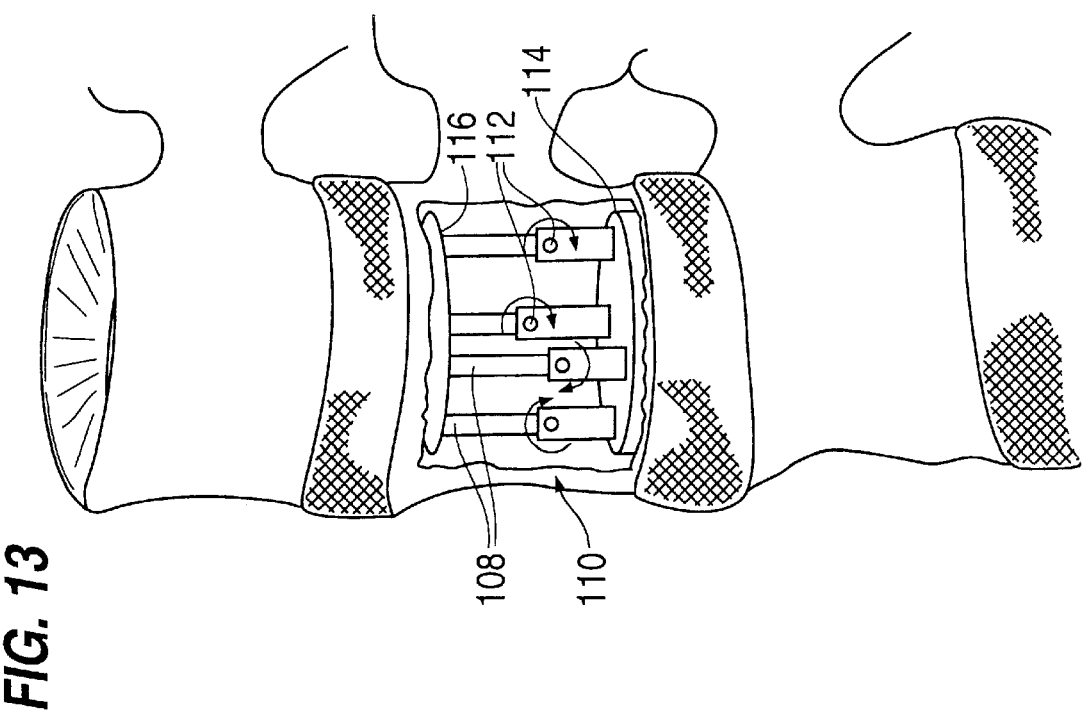
FIG. 13 is a schematic, cut-away, side view of a vertebral joint and shows a technique for adjusting the height of an adjustable member implanted in a superior vertebral body.

Once the fixation members are in place, the surgeon expands each adjustable member, one at a time, by placing a spreader device with a calibrated tensiometer between the first and second plates of the adjustable member. The surgeon applies distraction until the adjustable member is seated against the subchondral bone of the vertebral body and until the desired compression has been applied to the compressible member. The adjustment elements of the adjustable member are then secured. FIG. 13 shows rotation of the lock screws 112 of individual telescopic struts 108 to secure the struts at an appropriate height.

Figure 14:
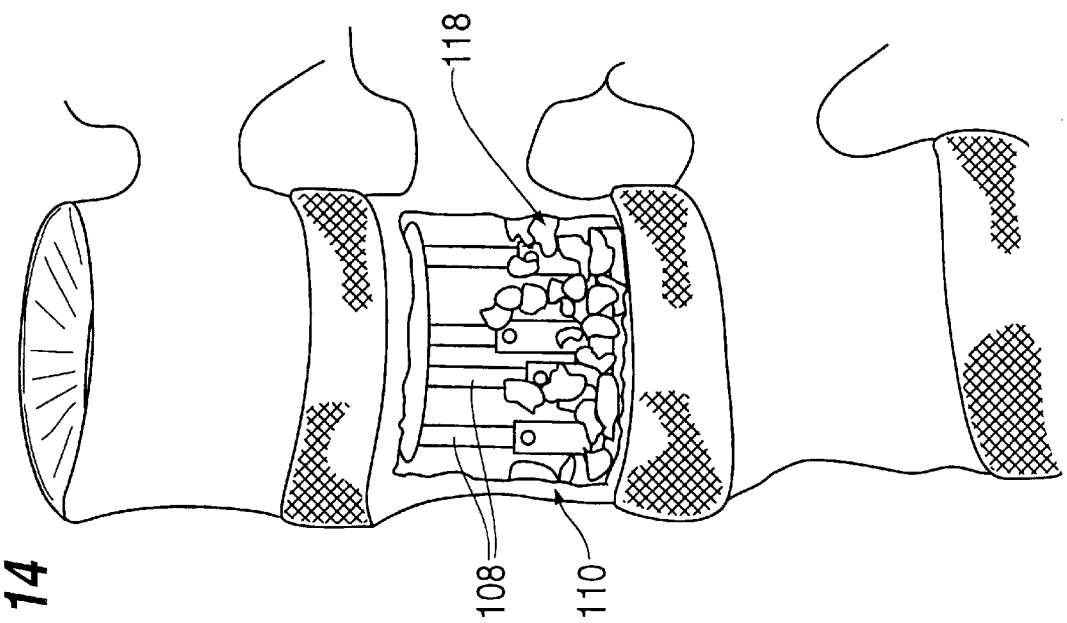
FIG. 14 is a schematic, cut-away, side view of a vertebral joint and shows a technique for bone grafting an adjustable member in a superior vertebral body.

The surgeon next packs cancellous bone grafts 118 around the struts of each adjustable member, as shown in FIG. 14. The growth of bone around the fixation member and into its porous surfaces secures the intervertebral prosthetic device in place, absent mechanical attachments typically used in conventional disc prostheses. The surgeon then replaces the cortical bone from the partial vertebrectomy procedure and secures it with a bone screw or bone cement.

*In certain clinical situations, as when there is poor bone healing or insufficient bone, the surgeon may elect to use bone cement to attach the fixation members to the vertebrae.

Additional advantages and modifications will readily occur to those skilled in the art. Therefore, the invention in its broader aspects is not limited to the specific details, and representative devices, shown and described herein. Accordingly, various modifications may be made without departing from the spirit or scope of the general inventive concept as defined by the appended claims and their equivalents.

What is claimed is:

1. An intervertebral prosthetic device for replacement of a nucleus pulposus of an intervertebral disc, comprising:
    a first intravertebral fixation member for fixation within a cavity of a first vertebral body, said first fixation member having a bone-contacting surface for positioning against subchondral bone of the first vertebral body; said first fixation member having at least one adjustable member for adjusting the length thereof;
    a second intravertebral fixation member for fixation within a cavity of a second vertebral body adjacent the first vertebral body, said second fixation member having a bone-contacting surface for positioning against subchondral bone of the second vertebral body; and
    a compressible member for positioning between said first fixation member and said second fixation member, said compressible member having a top plate connected to said first fixation member, a bottom plate connected to said second fixation member, and at least one compressible element therebetween that remains compressible after implantation, said compressible member further having an outer periphery less than or substantially equal to a diameter of the nucleus pulposus of the intervertebral disc.

2. A prosthetic device according to claim 1 wherein said first fixation member comprises a first support member and a first adjustable member that adjusts along a longitudinal axis of said first adjustable member.

3. A prosthetic device according to claim 2 wherein said second fixation member comprises a second support member and a second adjustable member that adjusts along a longitudinal axis of said second adjustable member.

4. A prosthetic device according to claim 3 wherein said first adjustable member and said second adjustable member each have at least one adjustment element that adjusts a height of a respective one of said first adjustable member and said second adjustable member.

5. A prosthetic device according to claim 4 wherein:
    each of said first adjustable member and said second adjustable member has a first plate and a second plate;
    said at least one adjustment element of said first adjustable member comprises a telescopic strut extending between said first plate and said second plate of said first adjustable member, and
    said at least one adjustment element of said second adjustable member comprises a telescopic strut extending between said first plate and said second plate of said second adjustable member.

6. A prosthetic device according to claim 4 wherein said at least one adjustment element has an exterior surface and a fin extending outward from said exterior surface.

7. A prosthetic device according to claim 1 wherein said compressible member comprises at least one spring.

8. A prosthetic device according to claim 1 wherein each said bone-contacting surface is porous.

9. An intervertebral prosthetic device for replacement of a nucleus pulposus of an intervertebral disc, comprising:
    a first intravertebral fixation member for fixation within a cavity of a first vertebral body, said first fixation member having an adjustable member and a support member, said adjustable member having a bone-contacting portion, an other portion for positioning against said support member, and at least one adjustment element for adjusting a distance between said bone-contacting portion and said other portion;
    a second intravertebral fixation member for fixation within a cavity of a second vertebral body adjacent the first vertebral body; and
    a compressible member positioned between said first fixation member and said second fixation member, said compressible member remaining compressible after implantation and being dimensioned to operably replace the nucleus pulposus of the intervertebral disc.

10. An intervertebral prosthetic device according to claim 9 wherein said second fixation member has an adjustable member and a support member, said adjustable member of said second fixation member having a bone-contacting portion, an other portion for positioning against said support member of said second fixation member, and at least one adjustment element for adjusting a distance between said bone-contacting portion of said second adjustable member and said other portion of said second adjustable member.

11. An intervertebral prosthetic device according to claim 9 wherein said second fixation member comprises a support member.

12. An intervertebral prosthetic device according to claim 9 wherein said device enables at least four degrees of relative motion between the first vertebral body and the second vertebral body.

13. An intervertebral prosthetic device for replacement of a nucleus pulposus of an intervertebral disc, comprising:
    a first intravertebral fixation member for fixation within a cavity of a first vertebral body and having a first longitudinal axis and at least one adjustment element that adjusts a length dimension of said first fixation member along said first longitudinal axis;

a second intravertebral fixation member for fixation within a cavity of a second vertebral body adjacent the first vertebral body; and a compressible member positioned between said first fixation member and said second fixation member and that remains compressible after implantation at the site of the replaced nucleus pulposus of the intervertebral disc.

14. A prosthetic device according to claim 13 wherein said first fixation member comprises an adjustable member and a support member, said adjustable member having a first bone-contacting plate and a second plate, said at least one adjustment element extending between said first bone-contacting plate and said second plate.

15. A prosthetic device according to claim 13 wherein said second fixation member has a second longitudinal axis and at least one adjustment element that adjusts a height of said second fixation member along said second longitudinal axis.

16. A prosthetic device according to claim 15 wherein each said at least one adjustment element has an exterior surface and at least one fin extending outward from said exterior surface.

17. A prosthetic device according to claim 15 wherein each said at least one adjustment element comprises a telescopic strut, and adjustment of each said telescopic strut pre-loads said compressible member.

18. A prosthetic device according to claim 14 wherein said second fixation member comprises an adjustable member and a support member, said adjustable member having a first bone-contacting plate and a second plate, said at least one adjustment element of said second fixation member extending between said first bone-contacting plate of said second fixation member and said second plate of said second fixation member.

19. A prosthetic device according to claim 18 wherein each said first bone-contacting plate has a concave, bone-contacting surface.

20. A prosthetic device according to claim 13 wherein said first fixation member has a first support member for placement between said at least one adjustment element and said compressible member, and said second fixation member comprises a second support member.

21. A prosthetic device according to claim 20 wherein at least one of said first support member and said second support member has a first surface facing away from said compressible member and a second surface facing toward said compressible member, and said first surface and said second surface are oblique.

22. An prosthetic device according to claim 20 wherein at least one of said first support member and said second support member has a circumference that varies in width.

23. A prosthetic device according to claim 13 wherein said compressible member comprises a top plate, a bottom plate, and at least one compressible element extending between said top plate and said bottom plate.

24. A prosthetic device according to claim 23 wherein:

said top plate has a first surface and a second surface, said first surface of said top plate being connectable to said first fixation member, and said bottom plate has a first surface and a second surface, said first surface of said bottom plate being connectable to said second fixation member.

25. A prosthetic device according to claim 23 wherein said at least one compressible element comprises at least one spring.

26. A prosthetic device according to claim 25 wherein said at least one spring comprises a coil spring having a non-uniform cross-sectional diameter.

27. A prosthetic device according to claim 25 wherein said at least one spring has a non-uniform pitch.

28. A prosthetic device according to claim 25 wherein said at least one spring comprises a plurality of coils each having a cross-section, and at least two of said plurality of coils have different cross-sections.

29. A prosthetic device according to claim 18 wherein:

said at least one adjustment element of said first fixation member comprises a plurality of adjustment elements, said plurality of adjustment elements extending between said first bone-contacting plate of said first fixation member and said second plate of said first fixation member, said at least one adjustment element of said second fixation member comprises a plurality of adjustment elements, said plurality of adjustment elements extending between said first bone-contacting plate of said second fixation member and said second plate of said second fixation member, said plurality of adjustment elements being spaced equidistant from each other.

30. A prosthetic device according to claim 29 wherein each of said plurality of adjustment elements is independently adjustable.

31. A prosthetic device according to claim 13 wherein said compressible member has a longitudinal axis and an outer periphery in a plane transverse to said longitudinal axis, a largest dimension of said outer periphery being less than or substantially equal to a diameter of a nucleus pulposus of an intervertebral disc.

32. A prosthetic device according to claim 23 wherein said compressible member has a longitudinal axis and an outer periphery in a plane transverse to said longitudinal axis, said outer periphery comprising a larger one of said periphery around said top plate and said periphery of said bottom plate.

33. A prosthetic device according to claim 13 wherein said compressible member has a longitudinal axis and an outer periphery in a plane transverse to said longitudinal axis, a largest dimension of said outer periphery being less than or substantially equal to 3.0 cm.

34. A prosthetic device according to claim 33 wherein said compressible member comprises a plurality of springs and said outer periphery circumscribes said plurality of springs.

35. A prosthetic device according to claim 13 wherein said first fixation member and said second fixation member each have a porous portion.

36. A prosthetic device according to claim 13 wherein said prosthetic device comprises a biocompatible metallic material.

37. A prosthetic device according to claim 36 wherein said metallic material comprises at least one of a titanium alloy and a cobalt-chromium alloy.

38. A prosthetic device according to claim 18 wherein each said adjustable member and each said support member comprise a ceramic material.

39. A prosthetic device according to claim 38 wherein said ceramic material is at least one of an aluminium oxide and a zirconium oxide.

40. A prosthetic device according to claim 13 wherein said compressible member has a height of approximately 1.5 cm and a diameter of approximately 2.0 to 3.0 cm.

41. A method of intervertebral disc replacement between a superior vertebra and an adjacent inferior vertebra in a spine, said method comprising:

excising a nucleus pulposus of an intervertebral disc while leaving intact an annulus fibrosis of the intervertebral disc;

performing partial vertebrectomies on the superior vertebra and the inferior vertebra;

implanting an inferior fixation member into a body of the inferior vertebra;

connecting a compressible member to said inferior fixation member;

implanting a superior fixation member into the superior vertebra and connecting said compressible member to said superior fixation member, at least one of said superior fixation member and said inferior fixation member being adjustable in a direction substantially parallel to the spine; and adjusting said at least one of said superior fixation member and said inferior fixation member to pre-load said compressible member.

42. An intervertebral prosthetic device for replacement of a nucleus pulposus of an intervertebral disc, comprising:

a first fixation member having a first portion for positioning against subchondral bone within a cavity of a first vertebral body, a second portion opposite said first portion, and a telescopic element extending between said first portion and said second portion to adjust a length dimension of said first fixation member;

a second fixation member having a bone-contacting portion for positioning against subchondral bone of a second vertebral body that is adjacent the first vertebral body; and a compressible member positioned between said second portion of said first fixation member and said second fixation member, said compressible member having at least one compressible element that compresses and expands in response to adjustment of said first fixation member.

43. A prosthetic device according to claim 29 wherein:

said plurality of adjustment elements of said first fixation member and said second fixation member are spaced between respective ones of said first bone-contacting plate and said second plate equidistant from each other.

* * * * *